United States Patent
Khamene et al.

(10) Patent No.: US 8,271,068 B2
(45) Date of Patent: Sep. 18, 2012

(54) METHOD FOR DYNAMIC ROAD MAPPING

(75) Inventors: Ali Khamene, Princeton, NJ (US); Frederik Bender, Denkendorf (DE); Wolfgang Wein, Princeton, NJ (US)

(73) Assignee: Siemens Aktiengesellschaft, München (DE)

( * ) Notice: Subject to any disclaimer, the term of this patent is extended or adjusted under 35 U.S.C. 154(b) by 1022 days.

(21) Appl. No.: 12/243,224

(22) Filed: Oct. 1, 2008

(65) Prior Publication Data

US 2009/0088632 A1   Apr. 2, 2009

Related U.S. Application Data

(60) Provisional application No. 60/976,920, filed on Oct. 2, 2007.

(51) Int. Cl.
*A61B 5/05* (2006.01)
(52) U.S. Cl. .................. 600/424; 600/433; 600/434
(58) Field of Classification Search .................. 600/424, 600/433, 434
See application file for complete search history.

(56) References Cited

U.S. PATENT DOCUMENTS

| | | | | |
|---|---|---|---|---|
| 5,287,276 | A * | 2/1994 | Crawford et al. | 378/4 |
| 6,560,354 | B1 * | 5/2003 | Maurer et al. | 382/131 |
| 2007/0237369 | A1 * | 10/2007 | Brunner et al. | 382/128 |
| 2010/0099979 | A1 * | 4/2010 | Schoonenberg et al. | 600/424 |

FOREIGN PATENT DOCUMENTS

WO   WO 2004/081877 A1 *  9/2004

OTHER PUBLICATIONS

D. Comaniciu, "Nonparametric Information Fusion for Motion Estimation," Real-Time Vision and Modeling Department, Siemens Corporation Research, IEEE Computer Society Conference on Computer Vision and Pattern Recognition 2003, pp. 1-8.

Selen Atasoy, Martin Groher, Darko Zikic, Ben Glocker, Tobias Waggershauser, Marcus Pfister and Nassir Navab, "Real-Time Respiratory Motion Tracking: Roadmap Correction for Hepatic Artery Catheterizations," Society of Photo-Optical Instrumentation Engineers 2008, pp. 1-9.

* cited by examiner

*Primary Examiner* — Brian Casler
*Assistant Examiner* — Daniel Huntley
(74) *Attorney, Agent, or Firm* — Donald B. Paschburg; F. Chau & Associates, LLC (57) ABSTRACT

A method of determining a three-dimensional (3D) position of a catheter tip includes: compensating a 2D position of the tip of the catheter for respiratory motion to generate a compensated 2D catheter position, generating weighted sample points around the compensated 2D catheter position, determining correspondent points of the weighted sample points in a 3D image, computing a weighted mean and a weighted covariance of each correspondent point, and determining the 3D position of the catheter tip in the 3D image from a fusion of the weighted means and weighted covariances.

20 Claims, 4 Drawing Sheets

METHOD FOR DYNAMIC ROAD MAPPING

CROSS-REFERENCE TO RELATED APPLICATIONS

This application claims priority to U.S. Provisional Application No. 60/976,920, filed on Oct. 2, 2007, the disclosure of which is incorporated by reference herein.

BACKGROUND OF THE INVENTION

1. Technical Field

The present disclosure relates to the dynamic road mapping of vascular system, and more particularly to methods for guiding a catheter through a dynamically mapped vessel.

2. Discussion of Related Art

Minimally invasive catheter-guided interventions play an important role in hospitals all over the world. A catheter is a medical device which may be introduced into a body channel or blood vessel for a variety of purposes. For example, one type is known as an intra-aortic balloon catheter which is used for cardiac assistance. Such catheters are frequently introduced into the body through the femoral artery because of the large diameter and accessibility of that artery. After insertion into the femoral artery, the distal end of the catheter can be pushed through the appropriate blood vessels to the location to be treated, e.g. an occluded blood vessel near the heart. The catheter may have a proximal end extending outside the body by which a distal end is manipulated and maneuvered. Since the path along which the catheter passes is frequently tortuous, the task of guiding and positioning the catheter is often difficult. It is sometimes necessary to remove the first catheter and insert a second catheter in its place. Further, once the distal end of the catheter reaches its desired location, it is often improperly positioned or extends angularly in the wrong direction, thus precluding the effective use of the catheter.

A 3D computed tomography angiography (CTA) scan of the patient may be taken in advance of the intervention to better plan the intervention, evaluate the risk of the planned intervention, or adjust the current diagnosis. During the intervention, surgeons may rely on two-dimensional (2D) fluoroscopic images, rather than 3D images. Bone structures and vessels (if a contrast agent is added) may be visualized in the fluoroscopic images. The 2D fluoroscopic images are often of low resolution. However, the low resolution images can be enhanced by high resolution Digital Subtraction Angiography (DSAs), where only vessel structure are visible.

However, in difficult interventions, even the enhanced 2D images may not be adequate. Further, blood vessel overlap in the projection images can make it difficult to navigate the catheter to the right position. Thus, there is a need for methods of guiding a catheter that can determine and incorporate the 3D position of the catheter.

SUMMARY OF THE INVENTION

An exemplary embodiment of the present invention include a method of determining a three-dimensional (3D) position of a catheter tip. The method includes: compensating a 2D position of the tip of the catheter for respiratory motion to generate a compensated 2D catheter position, generating weighted sample points around the compensated 2D catheter position, determining correspondent points of the weighted sample points in a 3D image, computing a weighted mean and a weighted covariance of each correspondent point, and determining the 3D position of the catheter tip in the 3D image from a fusion of the weighted means and weighted covariances.

The uncompensated 2D position may be derived from a 2D fluoroscopic sequence depicting the catheter and the method may further include: motion compensating an image of the 2D sequence using the compensated 2D catheter position, and overlaying a 3D vessel tree of the 3D image with the motion compensated image using the determined 3D position. Overlaying the 3D vessel tree onto the 2D motion compensated (static) fluoroscopic sequence in this way can enable better guidance of the catheter.

The compensating of the 2D position may include: selecting a region in the first image in which the catheter is visible and has a distinguishable shape as a template, determining a difference between a position of a matching region in a second image of the sequence and the position of the template to determine a respiratory motion displacement, and subtracting the respiratory motion displacement from the uncompensated 2D position.

The determining of the correspondent points of the weighted sample points in the 3D image may include back-projecting each weighted sample point as a 3D line. The generating of the weighted sample points around the compensated 2D catheter position may include: generating modified displacements from the respiratory motion displacement, determining sample points around the compensated 2D catheter position based on the modified displacements, and applying weights to each sample point based on a result of a cost function associated with the compensation of the respiratory motion. The cost function may be evaluated using the modified displacements.

The weights may be generated by: evaluating the cost function, normalizing results of the cost function, and deriving the weights from the normalized results. The weighted mean and the weighted covariance of each correspondent point may be based on a reciprocal of the cost function. The determining of the 3D position of the catheter tip in the 3D image from a fusion of the weighted means and weighted covariances may be fused using Variable-Bandwidth Density-Based Fusion. The back-projecting may be performed via a projection matrix. The projection matrix may be generated by aligning a Digital Subtraction Angiography (DSA) image with a 3D vessel model. The determining of the 3D position of the catheter tip in the 3D image from a fusion of the weighted means and weighted covariances may include: obtaining a common mean from information of the fusion and determining a point on a vessel in the 3D image that is closest to the common mean. The method may further include using the determined 3D position to guide a catheter.

An exemplary embodiment of the present invention includes a method of guiding a catheter in a vessel. The method includes: registering a Digital Subtraction Angiography (DSA) image with a 3D vessel model to generate a projection matrix, detecting a catheter tip position in a 2D image, compensating for motion in the catheter tip position based on the 2D image and a reference 2D image, generating weighted sample points around the compensated catheter tip position, determining correspondences of the weighted sample points in the 3D vessel model, selecting one of the correspondences based on an uncertainty of the registration and the compensation, and guiding the catheter using the selected correspondence.

The detecting of the catheter tip position may include using one of a magnetic tracking or optical tracking. The 2D image may include an image from a fluoroscope. The DSA image and the 3D vessel model may be derived from a 3D computed tomography angiography image. The catheter tip position may be determined from a first image of a sequence of 2D images. The compensating may include: selecting a region in the first image in which the catheter is visible and has a distinguishable shape as a template, determining a difference between a position of a matching region in a second image of the sequence and the position of the template to determine a respiratory motion displacement, and subtracting the respiratory motion displacement from the catheter tip position.

An exemplary embodiment of the present invention includes a method of determining a three-dimensional (3D) position of a catheter tip including: compensating a 2D position of a catheter tip for motion to generate a compensated 2D catheter position, generating sample points around the compensated 2D catheter tip position; determining correspondent points of the sample points in a 3D image, computing a weighted mean and a weighted covariance of each correspondent point, and determining the 3D position of the catheter tip in the 3D image from a fusion of the weighted means and weighted covariances.

BRIEF DESCRIPTION OF THE DRAWINGS

Exemplary embodiments of the invention can be understood in more detail from the following descriptions taken in conjunction with the accompanying drawings in which.

DETAILED DESCRIPTION OF THE EXEMPLARY EMBODIMENTS

In general, exemplary embodiments for systems and methods determining the 3D position of a catheter tip will now be discussed in further detail with reference to FIGS. 1-3b. This invention may, however, be embodied in different forms and should not be construed as limited to the embodiments set forth herein. Rather, these embodiments are provided so that this disclosure will be thorough and complete, and will fully convey the scope of the invention to those skilled in the art.

It is to be understood that the systems and methods described herein may be implemented in various forms of hardware, software, firmware, special purpose processors, or a combination thereof. In particular, at least a portion of the present invention may be implemented as an application comprising program instructions that are tangibly embodied on one or more program storage devices (e.g., hard disk, magnetic floppy disk, RAM, ROM, CD ROM, etc.) and executable by any device or machine comprising suitable architecture, such as a general purpose digital computer having a processor, memory, and input/output interfaces. It is to be further understood that, because some of the constituent system components and process steps depicted in the accompanying Figures may be implemented in software, the connections between system modules (or the logic flow of method steps) may differ depending upon the manner in which the present invention is programmed. Given the teachings herein, one of ordinary skill in the related art will be able to contemplate these and similar implementations of the present invention.

Exemplary embodiments of the present invention are concerned with the computation of a 3D position of a catheter tip in a 3D image based on its location in 2D images (e.g., frames of 2D fluoroscope images). However, when the 3D image is overlaid with each 2D image, if the 2D image moves, the 3D image moves as well, which may be distracting for a surgeon. Accordingly, exemplary embodiments of the present invention compensate for motion with respect to a reference frame. The result can then be aligned with the 3D image. In this way, position and orientation of the 3D model are less likely to change over time and the catheter tip is more likely to be visualized at its correct 3D position.

Figure 1:
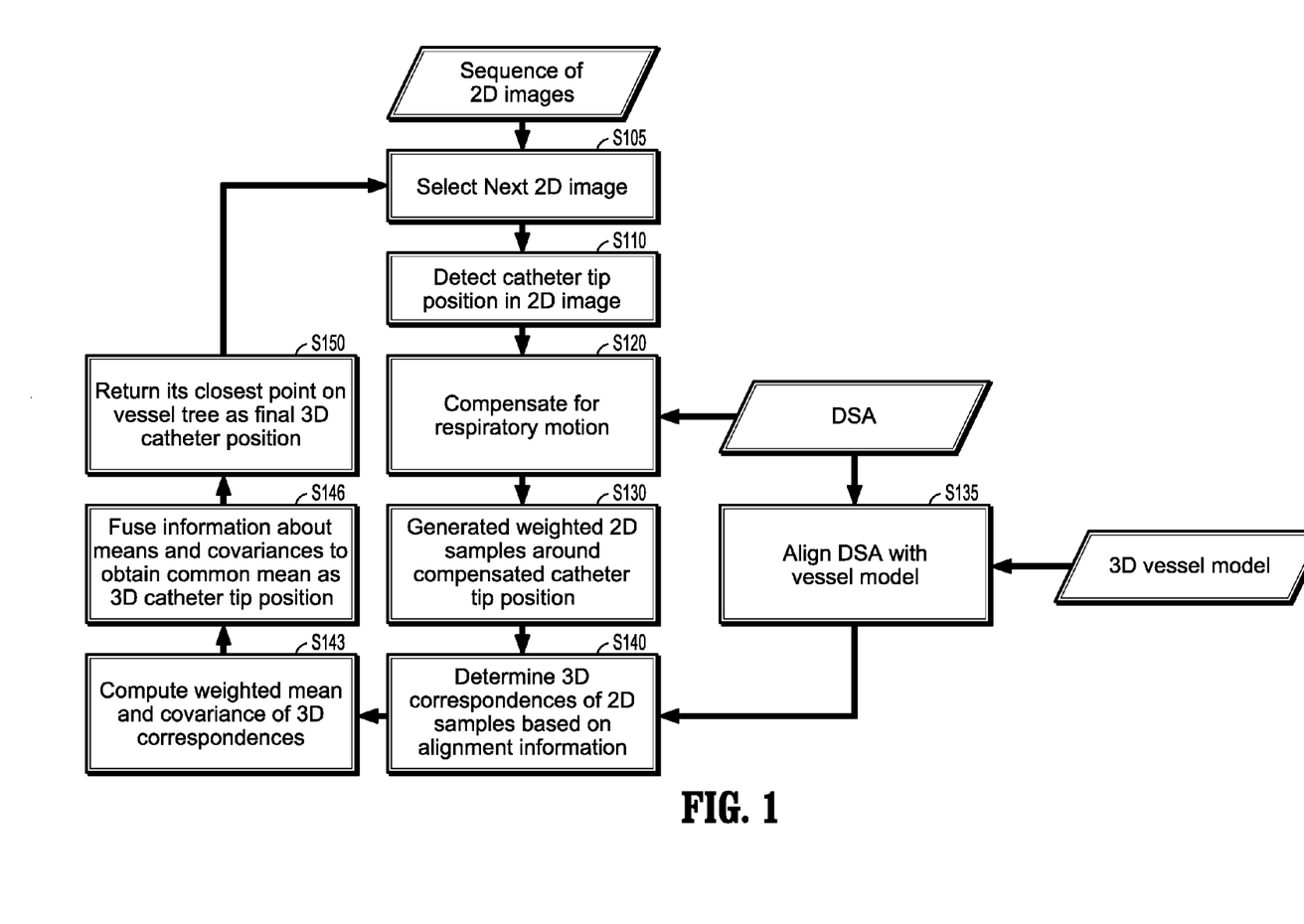
FIG. 1 illustrates a high-level flow-chart of a method of determining a 3D position of a catheter tip, according to an exemplary embodiment of the present invention.

FIG. 1 illustrates a high-level flow chart of a method of determining a 3D position of a catheter tip, according to an exemplary embodiment of the present invention. Referring to FIG. 1, a next one of a sequence of 2D images is selected (S105) and a 2D position of a catheter tip in the selected 2D image (e.g., a fluoroscopic image) is detected (S110). The position of the detected catheter tip is adjusted to compensate for the motion introduced by patient breathing using the 2D image and a Digital Subtraction Angiography (DSA) image (S120). Weighted sample points around the compensated tip position are determined (S130). The DSA image is aligned (e.g., a 2D/3D registration) with a 3D vessel model to generate alignment information (S135). The correspondences of the sample points in the 3D vessel model image are determined based on the alignment information (S140). The closest correspondent point on a vessel tree in the 3D vessel model may be determined to be the final 3D catheter position (S150).

Figure 3A:
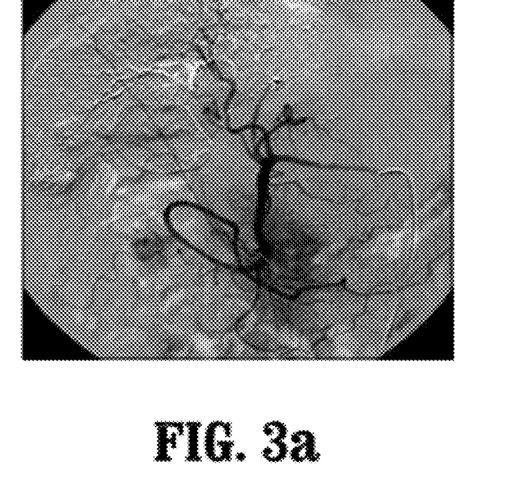
FIG. 3a illustrates an exemplary 2D DSA image.
Figure 3B:
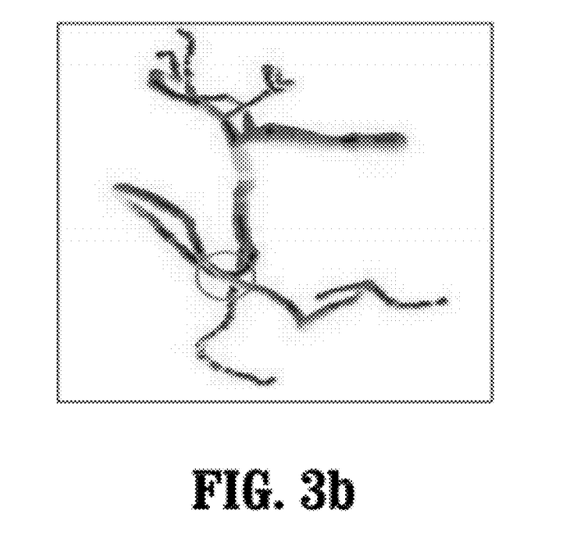
FIG. 3b illustrates an exemplary 3D vessel model.

FIG. 3a illustrates an exemplary DSA image and FIG. 3b illustrates an exemplary 3D vessel model, which may be used in the method of FIG. 1. The DSA image and the 3D vessel model may be extracted from CT or CTA data. CT is a method of medical imaging where a series of 2D X-Ray images are used to generate a three dimensional volume of a body or a body part. In CTA, a contrast agent is added, which makes vessels visible. When segmentation is applied, a 3D model of the blood vessel structures can be extracted. DSA is a special form of angiography, which improves the visibility of blood vessels. In DSA, two digital X-Ray images of the same part of the body are taken, a first image without a contrast agent and a second image without the contract agent. A subtraction is essentially performed on the two images and the resulting DSA image only shows vessels with any other background structures like bones, etc. Since there may be small patient movement in between the acquisition of the two images, techniques for spatial alignment or other preprocessing steps may be applied before the subtraction to the improve the quality of the DSA image.

Referring to step S110 of FIG. 1, the catheter tip position in the currently selected 2D image, denoted $x_i$, may be detected by various methods such as magnetic tracking, optical tracking, etc. In magnetic tracking, a magnet is attached to the catheter. In optical tracking, image processing methods are applied to detect the catheter tip position $x_i$.

Figure 2A:
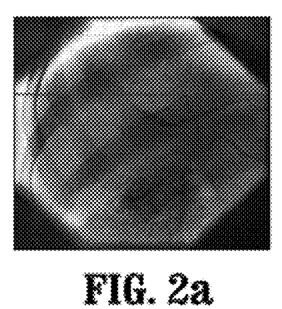
FIGS. 2a, 2b, and 2c illustrate exemplary catheter movement due to a patient's breathing.
Figure 2B:
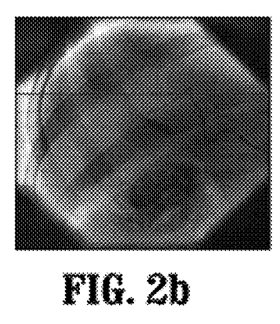
Figure 2C:
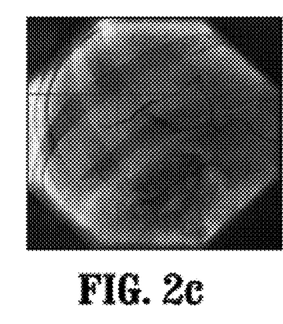

Referring to step S120 of FIG. 1, the detected catheter tip position $x_i$ is adjusted to compensate for motion introduced by patient breathing. For example, FIG. 2a-2c illustrate an example of respiratory motion introduced by patient breathing. To compensate for this motion, one can compute the displacement between the currently selected 2D image and a reference 2D image (e.g., the first 2D image) of the sequence of 2D images. There are two different types of motion that occur in-between two successive 2D images (e.g., frames.)

Figure 2D:
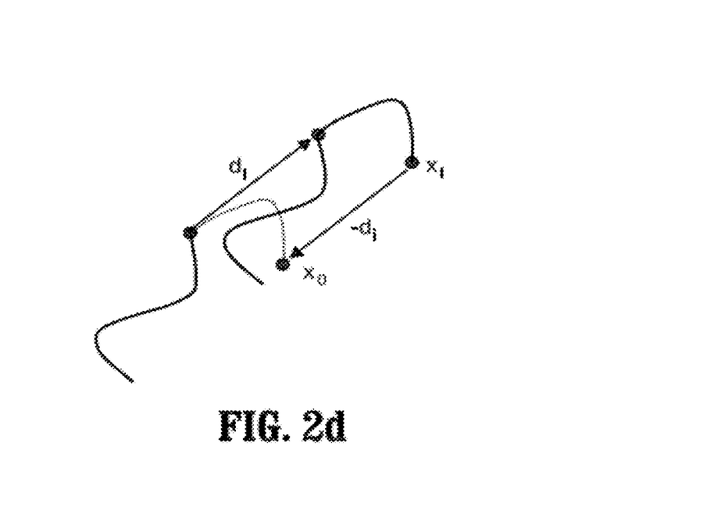
FIG. 2d illustrates an example of respiratory motion compensation, which may be used in the method of FIG. 1.

The first type of motion is introduced by the patient's breathing and the second type of motion is due to the physician moving the catheter inside a vessel. The breathing motion may be denoted by a displacement $\vec{d}_i$ and may be computed using a template based approach. In the template based approach, the user selects an image region in the reference 2D image where the catheter is visible and has a distinguishable shape. This region is used as a template and may be tracked over time using an intensity based similarity function or measure. The difference between the position of a matching region in the currently selected 2D image and the position of the selected template in the reference 2D image returns the respiratory motion displacement $\vec{d}_i$. Referring to FIG. 2d, the compensated catheter tip position, which may be $x_o$, may be obtained by subtracting the respiratory motion displacement $\vec{d}_i$ from the previously detected catheter tip position $x_i$.

However, the computed displacement $\vec{d}_i$ is merely an estimation. There may be a given uncertainty associated with the estimate. Depending on the above template chosen, this uncertainty may be smaller or larger in direction as compared to the other. For example, in a template that contains a horizontal line running from the very left border to the very right one, if this template is matched to an image that contains the same line but longer, this may yield a lower uncertainty for the y-direction, but a higher uncertainty in the x-direction. A more accurate estimate of this uncertainty may be computed when the values of the similarity function for multiple sampling points are compared.

Referring to step S130, weighted 2D sample points around the point of the compensated catheter tip position $x_o$, may be determined by modifying the computed displacement $\vec{d}_i$. By modifying (e.g., adding or subtracting values) the parameters of the computed displacement $\vec{d}_i$ within a small neighborhood, a set of samplings points $s_i$ around the compensated catheter tip position $x_o$ may be generated. The similarity function may be evaluated for each modified displacement $\vec{d}_{i_j}$. Each modified displacement $\vec{d}_{i_j}$ may be normalized to the interval [0,1] and used as a weight $w_j$ for each generated sampling point $S_{i_j}$. The similarity function may be a cost function.

Referring to step S135, the DSA image may be aligned (e.g., registered) with the 3D vessel model to generate alignment information (a projection matrix). The process of registration may involve a search for correct values for a set of parameters, which describe a transformation between the images to be registered. The type of transformation, and hence the number of parameters, depends on the dimension of the input data as well as the type of transformation. The transformation may be a Euclidean transformation, which includes three rotations around the three coordinate axis x, y, and z and three translations along the coordinate axis (e.g., six registration parameters). If $X=(x, y, z)^T$ denotes the original 3D point that needs to be translated, and $X_0=(x', y', z')^T$ the new, translated point, then a Euclidean transformation can be written according to the following equation 1:

$$X'=RX+t, \quad (1)$$

where R is a rotation matrix and t a translation vector with $t=t=(t_x, t_y, t_z)^T$. R can be based on Euler angles.

Using a pinhole projection model, the origin of a Euclidean coordinate system may be considered the center of a projection. An image plane may be defined as a plane parallel to the (X,Y)-plane with distance f (e.g., the image plane can be written as Z=f). The coordinate axis Z may also is also called the principal axis and the point where the principal axis meets the image plane may be called the principal point. A 3D point X in Euclidean space may be then mapped to a point x in the image plane such that x is the point where the image plane intersects a line joining X and the projection center C. This means that a point $X=(X_x, X_y, X_z)^T$ may be mapped to the point $x=(fX_x/X_z, fX_y, X_z)^T$ on the image place, which is a mapping from Euclidean 3D-space to Euclidean 2D-space. This mapping may be written in matrix form using homogenous coordinates as shown in the following equation 2:

$$P=K[1|0], \quad (2)$$

where P is called the camera projection matrix, which holds for x=PX, and where K is called the camera calibration matrix and has the form shown in the following equation 3:

$$\begin{pmatrix} f & 0 & 0 \\ 0 & f & 0 \\ 0 & 0 & 1 \end{pmatrix}. \quad (3)$$

The principal point may be assumed to be the origin of the coordinate system of the image plane and the number of image pixels per unit distance may be assumed to be the same in x- and y-directions. The former assumption leads to a vector $(p_x, p_y)^T$, which describes the principal point offset in the image plane coordinate frame. The latter assumption introduces two scaling factors, which may be multiplied with the focal distance f to generate the final calibration matrix, as shown in the following equation 4:

$$\begin{pmatrix} a_x & 0 & p_x \\ 0 & a_y & p_y \\ 0 & 0 & 1 \end{pmatrix}. \quad (4)$$

Since the pinhole camera model defines its own coordinate system, the world coordinate frame (where 3D points are expressed) needs to be related to the camera position and orientation. This may be done via a rotation R and a translation t, which lead to the final projection matrix as shown in the following equation 5:

$$P=K[R|t], \quad (5)$$

where R and t describe the position and orientation of the camera in terms of the Euclidean world coordinate system frame and K describes the internal camera settings. The final projection matrix P brings the DSA image and the 3D vessel model into spatial alignment.

It may be assumed that the reference 2D image has the same spatial location and orientation as the DSA image. The spatial relationship of the 3D vessel model and the currently selected 2D image i can be expressed via the projection matrix P. Referring to step S140 of FIG. 1, the correspondences of the sample points in the 3D vessel model may be determined based on the alignment information (e.g., the projection matrix P). For example, the correspondences may be determined by back-projecting each sample point as a 3D line via the projection matrix P, and searching for the closest vessel point on a vessel tree in the 3D vessel model (e.g., step S150). However, this may lead to an incorrect correspondence since the projection of different 3D points can yield the exact same point in 2D (e.g., both 3D points might have the same or a similar distance to the back-projected line). Accordingly, a statistical approach is introduced based on an evaluation of the registration accuracy and the uncertainty of the motion compensation.

Each of the weighted sample points $s_i$ may be back-projected to generate a set of 3D vessel points $S_i$. Since the ground truth of the 2D/3D registration may not be known, an uncertainty of P may be assumed that introduces an uncertainty to the 3D position of each of the 3D vessel points $S_i$.

The uncertainty may be computed by modifying the 6 registration parameters randomly with a given interval, evaluating an iterative closest point (ICP) cost function, and computing several sampling points $S_{i_j}$ around $S_i$ using the modified transformation $T_j$. An iterative closest point algorithm enables registration between two point sets X and Y. The closest point $y \in Y$ to a point $x \in X$ may be represented by the following equation 6:

$$CP(x, Y) = \underset{y \in Y}{\mathrm{argmin}}\, d(x, y) \qquad (6)$$

where d(x, y) is the Euclidean distance between the points x and y (e.g., $d(x, y) = \|x-y\|$). A closest point search can then be performed, which results in a set of correspondences $\{x_i \Leftrightarrow y_i\}$ of size N where $x_i \in X$ and $y_i \in Y$. After a first set of correspondences has been generated, the transformation between those sets may be computed by minimizing the mean-squares objective function shown in the following equation 7:

$$F(R, t) = \frac{1}{N} \sum_{i=1}^{N} \|Rx_i + t - y_i\|^2. \qquad (7)$$

The newly computed transformation parameters R and t can be used to transform the point set X. The sampling points $S_{i_j}$ may be weighted by the normalized reciprocal of the cost value function.

Referring to step S143, the weighted mean and covariance matrix of the sample points $S_{i_j}$ may be computed respectively according to the following equations 8 and 9:

$$X_i = \overline{S}_i = \frac{1}{\sum_{j=1}^{n} w_j} \sum_{j=1}^{n} w_j S_{i_j}, \qquad (8)$$

and $$C_i = \sigma s_i = \frac{1}{\sum_{j=1}^{n} w_{ji}} \sum_{j=1}^{n} w_j (S_{i_j} - \overline{S}_i)(S_{i_j} - \overline{S}_i)^T, \qquad (9)$$

where $w_j$ is the weight corresponding to transformation $T_j$, derived from the cost function evaluation. The weighted mean and covariance are computed for each $S_i$, and this information may then be fused as shown in step S146 of FIG. 1. The final 3D catheter tip location may be represented by the closest point on the vessel tree that corresponds to the fused information.

The fused information may be derived using a non-parametric approach, known as Variable-Bandwidth Density-Based Fusion (VBDF) that takes the uncertainty of the sample points $S_{i_j}$ into account to eliminate outliers (e.g., artificial seed points). In this approach, a density function is estimated for all measurements and an estimate for the location of the 3D catheter tip position is the density function's most significant mode.

The most significant mode may be detected using a method called variable-bandwidth mean shift. For gaussian kernels, mean shift is an iterative, hill-climbing approach, that moves a given point X towards a location with an equal or higher density in a local neighborhood, and converges to a location with zero gradient. Therefore, it is also called a mode-seeking algorithm. Variable-bandwidth is used to keep the algorithm nonparametric and to improve the kernel estimator by adapting the scale of the kernel. The bandwidth may be chosen based on the covariance matrix of each sample point $S_i$, and on a scaling factor α. This scaling factor α may be initialized with a large value as compared to the point spread of the measurements, and may be decreased iteratively over time. The resulting bandwidth matrix that is used to specify the density function may be represented by the following equation 10:

$$H_i = H(X_i) = C_i + \alpha^2 I \qquad (10)$$

where $C_i$ is the covariance matrix computed for sampling point $S_i$, and I is the identity matrix. The density function may be represented by the following equation 11:

$$f_V(X) = \frac{1}{n(2\pi)^{d/2}} \sum_{i=1}^{n} \frac{1}{|H_i|^{1/2}} \exp\left(-\frac{1}{2} D^2(X, X_i, H_i)\right)$$

where $D^2(X, X_i, H_i)$ is the Mahalanobis distance between sample point $X_i$ and point I, which may be represented by the following equation 12:

$$D^2(X, X_i, H_i) \equiv (X-X)^T H_i^{-1} (X-X). \qquad (12)$$

The variable-bandwidth mean shift vector that may be used to detect the most significant mode of $f_v$ for each scale may be represented by the following equation 13:

$$m_v(x) \equiv \left( H_h(x) \sum_{i=1}^{n} w_i(X) H_i^{-1} X_i \right) - X, \qquad (13)$$

where $H_h$ is the date-weighted harmonic mean of the bandwidth matrix and may represented by the following equation 14:

$$H_h(x) = (\Sigma k=1^n w_i(X) H_i^{-1})^{-1}. \qquad (14)$$

Each sample point $X_i$ may be associated with a weight $w_i$, which can be recomputed for each scale and may be represented by the following equation 15:

$$w_k() = \frac{\frac{1}{H_i^{1/2}} \exp\left(-\frac{1}{2} D^2(X, X_i, H_i)\right)}{\sum_{i=1}^{n} \left( \frac{1}{H_i^{1/2}} \exp\left(-\frac{1}{2} D^2(X, X_i, H_i)\right) \right)}, \qquad (15)$$

where the weights satisfy the condition $$\sum_{i=1}^{n} w_k(X) = 1.$$

If the initial bandwidth is chosen large enough (e.g., assign high value for α), a density function with only one mode is generated.

In a density function with only one mode, one can pick any random value for X and the mean shift algorithm will still converge to the desired mode. This position can then be used as an initial value for X at the next iteration with a decreased scale factor. These steps may be repeated until a scale factor of zero. The detected mode of this iteration is declared to be the most significant mode of the density function, and therefore, the final result for the fusion estimator. This adds an extension to the original VBDF, which includes information about the 3D catheter tip position of the previous frame, and the weight of the 2D point that was used to compute $S_i$ and accordingly $X_i$. This extension involves a modification of the weights $w_i$. Essentially, a higher rating is given to sample points $X_i$, which lie on the same or a connecting vessel branch as the catheter tip of the previous frame.

Figure 4:
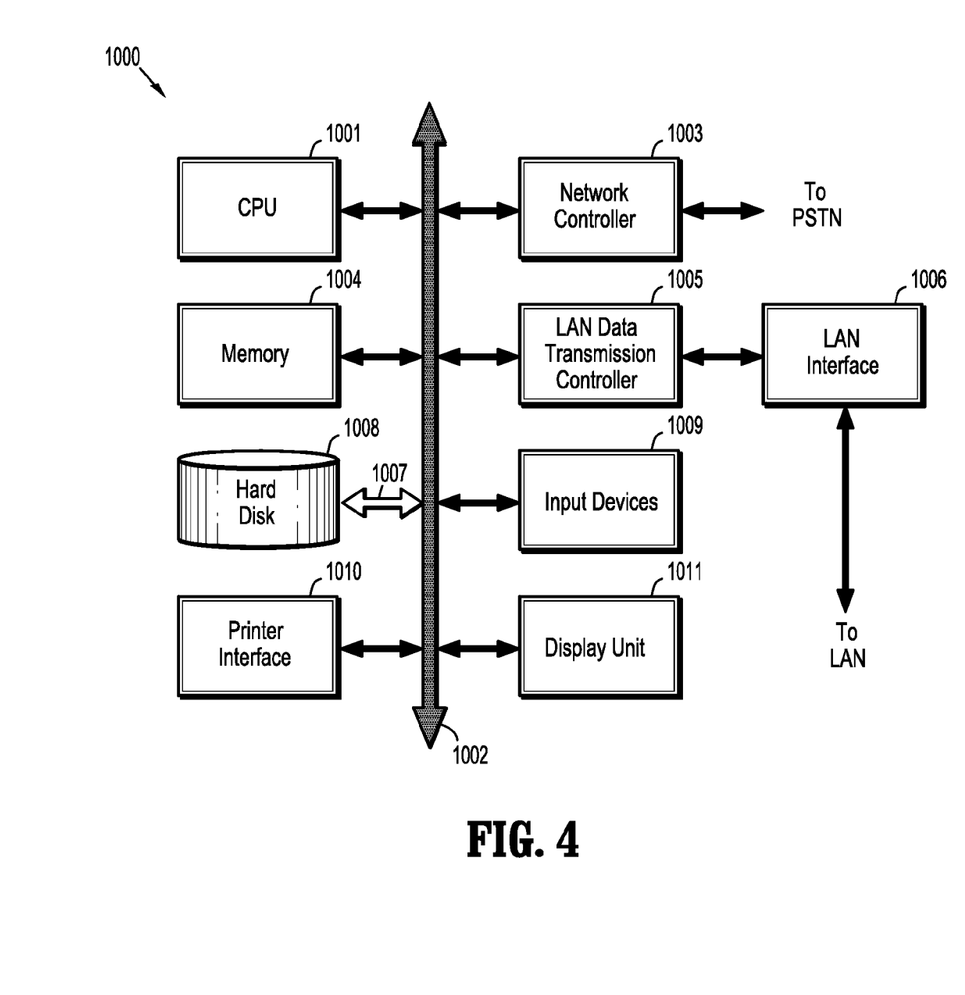
FIG. 4 shows an example of a computer system capable of implementing the method and apparatus according to embodiments of the present disclosure.

FIG. 4 shows an example of a computer system which may implement a method and system of the present disclosure. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Although the illustrative embodiments have been described herein with reference to the accompanying drawings, it is to be understood that the present invention is not limited to those precise embodiments, and that various other changes and modifications may be affected therein by one of ordinary skill in the related art without departing from the scope or spirit of the invention. All such changes and modifications are intended to be included within the scope of the invention.

What is claimed is:

1. A method of determining a three-dimensional (3D) position of a catheter tip, the method comprising:
   compensating a 2D position of the tip of the catheter for respiratory motion to generate a compensated 2D catheter position;
   generating weighted 2D sample points around the compensated 2D catheter position;
   determining 3D correspondent points of the weighted sample points in a 3D image;
   computing, with a processor, 3D sample points around each 3D correspondent point using a modified transformation derived from evaluating an iterative closest point cost function;
   computing, with a processor, a weighted mean of each 3D correspondent point from the corresponding 3D sample points using a weight corresponding to the modified transformation;
   computing, with a processor, a weighted covariance of each 3D correspondent point based on a difference between the corresponding weighted mean and the corresponding 3D sample points; and
   determining the 3D position of the catheter tip in the 3D image from a fusion of the weighted means and weighted covariances.

2. The method of claim 1, wherein the uncompensated 2D position is derived from a 2D fluoroscopic sequence depicting the catheter and the method further comprises:
   motion compensating an image of the 2D sequence using the compensated 2D catheter position; and
   overlaying a 3D vessel tree of the 3D image with the motion compensated image using the determined 3D position.

3. The method of claim 2, wherein the compensating comprises:
   selecting a region in a first image in which the catheter is visible and has a distinguishable shape as a template;
   determining a difference between a position of a matching region in a second image of the sequence and the position of the template to determine a respiratory motion displacement; and
   subtracting the respiratory motion displacement from the uncompensated 2D position.

4. The method of claim 1, wherein determining correspondent points of the weighted sample points in the 3D image comprises back-projecting each weighted sample point as a 3D line.

5. The method of claim 3, wherein generating weighted sample points around the compensated 2D catheter position comprises:
   generating modified displacements from the respiratory motion displacement;
   determining sample points around the compensated 2D catheter position based on the modified displacements; and
   applying weights to each sample point based on a result of a cost function associated with the compensation of the respiratory motion.

6. The method of claim 5, wherein the cost function is evaluated using the modified displacements.

7. The method of claim 6, wherein the weights are generated by:
   evaluating the cost function;
   normalizing results of the cost function; and
   deriving the weights from the noimalized results.

8. The method of claim 5, wherein the weighted mean and the weighted covariance of each correspondent point is based on a reciprocal of the cost function associated with the compensation of the respiratory motion.

9. The method of claim 1, wherein determining the 3D position of the catheter tip in the 3D image from a fusion of the weighted means and weighted covariances are fused using Variable-Bandwidth Density-Based Fusion.

10. The method of claim 4, wherein the back-projecting is performed via a projection matrix.

11. The method of claim 10, wherein the projection is generated by aligning a Digital Subtraction Angiography (DSA) image with a 3D vessel model.

12. The method of claim 1, wherein determining the 3D position of the catheter tip in the 3D image from a fusion of the weighted means and weighted covariances:

obtaining a common mean from information of the fusion; and determining a point on a vessel in the 3D image that is closest to the common mean.

13. The method of claim 1, further comprising using the determined 3D position to guide a catheter.

14. A method of guiding a catheter in a vessel, the method comprising:

registering, with a processor, a Digital Subtraction Angiography (DSA) image with a 3D vessel model to generate a projection matrix;

detecting a 2D catheter tip position in a 2D image;

compensating for motion in the catheter tip position based on the 2D image and a reference 2D image;

generating weighted 2D sample points around the compensated catheter tip position;

determining correspondent 3D points of he weighted 2D sample points in the 3D vessel model;

selecting one of the correspondent 3D points based on an uncertainty of the registration and the compensation; and guiding the catheter using the selected correspondent 3D point.

15. The method of claim 14, wherein the detecting the catheter tip position comprises using one of a magnetic tracking or optical tracking.

16. The method of claim 14, wherein the 2D image comprises an image from a fluoroscope.

17. The method of claim 14, wherein the DSA image and the 3D vessel model are derived from a 3D computed tomography angiography image.

18. The method of claim 14, wherein the catheter tip position is determined from a first image of a sequence of 2D images.

19. The method of claim 18, wherein the compensating comprises:

selecting a region in the first image in which the catheter is visible and has a distinguishable shape as a template;

determining a difference between a position of a matching region in a second image of the sequence and the position of the template to determine a respiratory motion displacement; and subtracting the respiratory motion displacement from the catheter tip position.

20. A program storage device readable by machine, tangibly embodying a program of instructions executable by the machine to perform method steps of determining a three-dimensional (3D) position of a catheter tip, the method steps comprising:

compensating a 2D position of a catheter tip for motion to generate a compensated 2D catheter position;

generating first sample points around the compensated 2D catheter tip position;

determining correspondent points of the first sample points in a 3D image;

computing second sample points around each correspondent point using a modified transformation derived from evaluating an iterative closest point cost function;

computing a weighted mean for each correspondent point from the corresponding second sample points using a weight corresponding to the modified transformation;

computing a weighted covariance of each correspondent point based on a difference between the corresponding weighted mean and the corresponding second sampling points; and determining the 3D position of the catheter tip in the 3D image from a fusion of the weighted means and weighted covariances.

* * * * *